US010539568B2

(12) United States Patent
Lattanzio et al.

(10) Patent No.: US 10,539,568 B2
(45) Date of Patent: Jan. 21, 2020

(54) RP-HPLC ANALYSIS OF COMPLEX POLYPEPTIDE MIXTURES

(71) Applicant: Chemi S.P.A., Cinisello Balsamo (IT)

(72) Inventors: Maria Lattanzio, Cinisello Balsamo (IT); Aureliano Gaiassi, Cinisello Balsamo (IT); Andrea Stevenazzi, Cinisello Balsamo (IT)

(73) Assignee: CHEMI, S.P.A., Cinisello Balsamo (IT)

( * ) Notice: Subject to any disclaimer, the term of this patent is extended or adjusted under 35 U.S.C. 154(b) by 45 days.

(21) Appl. No.: 15/351,599

(22) Filed: Nov. 15, 2016

(65) Prior Publication Data
US 2017/0146547 A1 May 25, 2017

(30) Foreign Application Priority Data
Nov. 23, 2015 (EP) .................................... 15195917

(51) Int. Cl.
| | |
|---|---|
| G01N 33/68 | (2006.01) |
| B01D 15/32 | (2006.01) |
| G01N 30/74 | (2006.01) |
| G01N 30/88 | (2006.01) |
| G01N 33/94 | (2006.01) |
| G01N 33/48 | (2006.01) |

(52) U.S. Cl.
CPC ....... *G01N 33/6803* (2013.01); *B01D 15/325* (2013.01); *G01N 30/74* (2013.01); *G01N 30/88* (2013.01); *G01N 33/94* (2013.01); *G01N 2030/8831* (2013.01)

(58) Field of Classification Search
CPC .... G01N 33/6803; G01N 33/68; G01N 33/50; G01N 33/48; B01D 15/325; B01D 15/32; B01D 15/26; B01D 15/08

USPC ........................................................ 436/86
See application file for complete search history.

(56) References Cited

U.S. PATENT DOCUMENTS

| | | |
|---|---|---|
| 3,849,550 A | 11/1974 | Arnon et al. |
| 5,800,808 A | 9/1998 | Konfino et al. |
| 2014/0045740 A1 | 2/2014 | Glajch et al. |

FOREIGN PATENT DOCUMENTS

| | | |
|---|---|---|
| CN | 104297404 A | 1/2015 |
| WO | 1995031990 A1 | 11/1995 |
| WO | 2003029276 A2 | 4/2003 |

(Continued)

OTHER PUBLICATIONS

Fridkis-Hareli et al, Direct binding of myelin basic protein and synthetic copolymer I to class II major histocompatibility complex molecules on living antigen-presenting cells-specifically and promiscuity, Proc. Natl., Acad. Sci. USA. May 1994, vol. 91, pp. 4872-4876. (Year: 1994).*

(Continued)

*Primary Examiner* — Christine T Mui
(74) *Attorney, Agent, or Firm* — Silvia Salvadori, P.C.; Silvia Salvadori

(57) ABSTRACT

The present invention relates to reversed phase high-performance liquid chromatography (HPLC) methods useful for the characterisation of glatiramer acetate or similar polypeptide mixtures. The method described herein can distinguish glatiramer acetate from non-conforming copolymers and may be used to choose batches of glatiramer acetate suitable for pharmaceutical use.

13 Claims, 3 Drawing Sheets

(56) References Cited

FOREIGN PATENT DOCUMENTS

| WO | 2008006026 | A1 | 1/2008 |
|---|---|---|---|
| WO | 2009129018 | A1 | 10/2009 |
| WO | 2012123959 | A2 | 9/2012 |

OTHER PUBLICATIONS

Di Paola, M. Characterization of glatiramer acetate c-terminal heterogeneity 1-19 Biosimilar 2015.

Espinosa-De La Garza, et al., "Analysis of therapeutic proteins and peptides using multiangle light scattering coupled to ultra high performance liquid chormatography", URL: http://onlinelibrary.wiley.com/doi/10.1002/ssc.201400863 full (Feb. 5, 2016).

Haim V., et al., "The glatiramoid class of immunomodulator drugs", Expert Opinion on Pharmacotherapy, vol. 10, No. 4, Mar. 25, 2009, pp. 657-668.

Rogstad S., et al., "Modern analytic for synthetically derived complex drug substances: NMR, AFFF-MALS, and MS tests for glatiramer acetate", Anaylytica and Bioanalytical Chemistry, vol. 407, No. 29, Oct. 12, 2015, pp. 8647-8659.

Schlautman J. et al, "Multidimensional protein fractionation using ProteomeLab PF 2D (TM) for profiling amyotrophic lateral sclerosis immunity: A preliminary report", Proteome Science, Biomed Central, vol. 6, No. 1, Sep. 12, 2008, p. 26.

Search Report of EP15195917.8 dated May 9, 2015.

Teitelbaum, D., et al., "Suppression of experimental allergic encephalomyelitis by a synthetic polypeptide", Eur. J. Immunol, 1971 1:242-248.

Varkony H., et al. "The glatiramoid class of immunomodulator drugs", Expert Opin Pharmacother. (2009) 10(4):657-668.

Vergote V., et al., "Quality specifications for peptide drugs: a regulatory-pharmaceutical approach", J. Pept. Sci. 2009, 15:697-710.

Eggn, et al., "Control Strategies for Synthetic Therapeutic Peptide APIs," Pharmaceutical Technology, Mar. 2014 109668-109672.

Pasch, et al., "HPLC of Polymers", 1999, 70-88.

\* cited by examiner

RP-HPLC ANALYSIS OF COMPLEX POLYPEPTIDE MIXTURES

This U.S. non-provisional application claims priority to and the benefit of European Patent Application No. 15195917.8 filed on Nov. 23, 2015, the content of which is incorporated herein by reference in its entirety.

The present invention relates to reversed phase high-performance liquid chromatography (RP-HPLC) methods useful for the characterisation of glatiramer acetate or similar polypeptide mixtures. The method described herein can distinguish glatiramer acetate from non-conforming copolymers and may be used to choose batches of glatiramer acetate suitable for pharmaceutical use.

BACKGROUND OF THE INVENTION

Glatiramoids are a family of synthetic copolymers containing four amino acids: L-glutamic acid, L-alanine, L-lysine and L-tyrosine, in a defined molar ratio (Varkony et al. 2009). Glatiramer acetate (GA) is a member of the glatiramoid family, and it is the active pharmaceutical ingredient of the commercially available medicine Copaxone® (Teva Pharmaceutical Industries Ltd., Israel), indicated for the treatment of patients with relapsing forms of multiple sclerosis.

According to the product labelling, GA consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of GA ranges from 5,000 to 9,000 daltons.

Chemically, GA is designated L-glutamic acid polymer with L-alanine, L-lysine and L-tyrosine, acetate (salt). Its structural formula is:

(Glu,Ala,Lys,Tyr)$_x$·xCH$_3$COOH

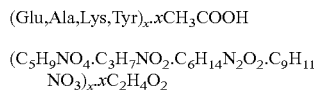

CAS—147245-92-9

(NDA 020622/S-089 FDA Approved Labelling Text dated Jan. 28, 2014)

GA is synthesised via amino acid polymerisation followed by a subsequent cleavage or partial depolymerisation step. Because of the stochastic nature of polymerisation and cleavage reactions, the polypeptides obtained by this process vary in sequence, length and molecular weight (MW), resulting in a characteristic molecular weight distribution (MWD) that spans from about 2,500 to 20,000 daltons.

Various analytical methods useful for characterising glatiramer acetate or similar polypeptide mixtures are described in patent literature and some regulatory documents (including "citizen petitions"). These methods include amino acid analysis, size exclusion chromatography, circular dichroism, reversed-phase liquid chromatography, capillary electrophoresis, peptide mapping, Edman sequencing, analysis of C- and N-terminal signatures (e.g. C-terminal diethylamide and N-terminal pyroglutamate).

The present invention is based on a new and original chromatographic method, which can distinguish glatiramer acetate from non-conforming copolymers and may be used, together with other quality attributes, to choose batches of glatiramer acetate suitable for pharmaceutical use.

DEFINITIONS

Figure 1:
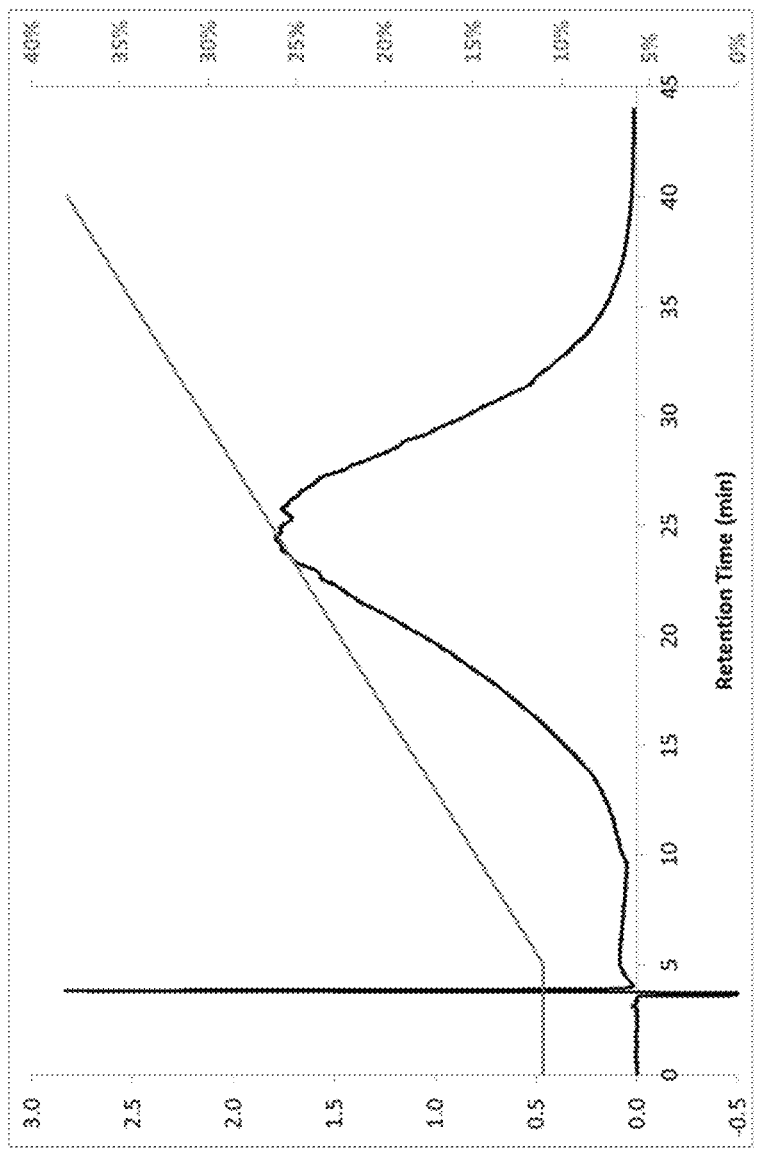
FIG. 1. RP-HPLC analysis of glatiramer acetate (linear gradient; solvent A: water with TFA 0.10%; solvent B: acetonitrile with TFA 0.08%; gradient: 10% B for 5 min, then 10 to 40% B in 35 minutes).

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The terms "approximately" and "about" herein refers to the range of the experimental error, which may occur in a measurement.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients and/or steps which materially affects the basic and novel characteristics of the invention are included (optional excipients may be thus included).

The terms "consists of", "consisting of" are to be construed as a closed term.

The terms "sameness" or "sameness criteria" herein refer to those physical, chemical and/or biological drug substance(s) attributes that, according to a regulatory agency (for example, the U.S. Food and Drug Administration), should be compared to prove that a generic drug product contains the same active ingredient(s) as the innovator product. Taking Copaxone as an example, the FDA concluded that an applicant for generic glatiramer acetate injection can demonstrate active ingredient sameness as to the following four criteria: (1) Fundamental reaction scheme; (2) Physicochemical properties including composition; (3) Structural signatures for polymerization and depolymerization; and (4) Results in a biological assay.

The term "non-conforming copolymer" herein refers to a copolymer, or mixture of polypeptides, which does not meet the "sameness criteria" compared to the innovator product. The term "glatiramoid" herein refers to a heterogeneous mixture of polypeptides containing four naturally occurring amino acid residues (L-glutamic acid, L-alanine, L-tyrosine, L-lysine) in a specified molar ratio, i.e. wherein the molar fraction range of L-glutamic acid is 0.129-0.153, that of L-alanine is 0.392-0.462, that of L-tyrosine is 0.086-0.100 and of L-lysine is 0.300-0.374.

The term "mixture of polypeptides" herein also includes the possible pharmaceutically acceptable salts, particularly the acetate.

The term "pharmaceutically acceptable salts" herein refers to those salts which possess the biological effectiveness and properties of the salified compound and which and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, acetate, trifluoroacetate, 2-naphthalenesulphonate, and para-toluenesulphonate. Further information on pharmaceutically acceptable salts can be found in *Handbook of pharmaceutical salts*, P. Stahl, C. Wermuth, WILEY-VCH, 127-133, 2008, herein incorporated by reference.

DESCRIPTION OF THE INVENTION

The present invention describes an analytical method useful for characterising glatiramoids and assessing the identity of glatiramer acetate. The method described herein can distinguish glatiramer acetate from non-conforming copolymers and may be used to choose batches of glatiramer acetate suitable for pharmaceutical use.

In the method of the invention, glatiramoids and glatiramer acetate may be prepared following the manufacturing processes already described (Teitelbaum et al. 1971, U.S. Pat. Nos. 3,849,550, 5,800,808), herein incorporated by reference, which include the following steps:

Step (1): polymerisation of the protected amino acid precursors (N-carboxyanhydrides) to obtain a protected copolymer;

Step (2): deprotection of gamma-benzyl glutamate, using hydrobromic acid in acetic acid, and partial depolymerisation;

Step (3): deprotection of N-trifluoroacetyl lysine in aqueous piperidine.

The resulting water-soluble copolymer may be then purified through multiple diafiltration or ultrafiltration steps and freeze dried to obtain a batch of solid glatiramoid or glatiramer acetate. Because of the stochastic nature of polymerisation and cleavage reactions, GA is a complex mixture of polypeptides which vary in chain length (molecular weight), chemical composition and sequence.

Whereas homopolymers (i.e. polymers that contain only a single type of repeat unit) are characterised by their molar mass distribution alone, and a single chromatographic method may be sufficient for analysing their relevant physicochemical attributes, copolymers (such as glatiramer acetate) are more complex and should be characterised by orthogonal separation techniques, such as size exclusion chromatography, ion exchange chromatography, capillary electrophoresis, reversed phase liquid chromatography. Orthogonal methods may detect differences in structure or composition not observed by looking at molar mass distribution and building block composition alone.

Chromatography is defined as a procedure by which solutes are separated by a differential dynamic distribution process in a system consisting of two phases, one of which is the mobile phase and the other the stationary phase.

Reversed-phase high-performance liquid chromatography (RP-HPLC) is a high-resolution and versatile approach for the analysis of peptides and peptide mixtures. Examples in the published literature and in compendial monographs include chromatographic identification tests, impurity testing, and chromatographic separation of complex peptide mixtures, such as tryptic digests (peptide mapping) (Vergote et al. 2009, Eggen et al. 2014).

In RP-HPLC, the stationary phase typically consists of a non-polar organic phase chemically bound to silica gel, such as a C4-bonded silica gel (where the surface silanol groups are derivatized with butyl residues), or other supporting materials. The mobile phase is normally polar (aqueous) and its strength can be varied over time by changing its composition (usually the ratio between a more polar solvent and a less polar solvent, such as water and acetonitrile, respectively).

Adsorption interactions between macromolecules (such as polypeptides) and stationary phase are based on a multiple attachment mechanism. A polymer chain can migrate only if all its constituting units are in the mobile phase. Therefore, the macromolecule will be retained in the stationary phase as long as one of its repeating units is adsorbed. Assuming independent adsorption-desorption equilibrium for each unit, for weak eluents and long polymer chains there will be always a repeating unit interacting with the packing material. Accordingly, the macromolecule will be retained until the strength of the mobile phase (which is determined by its composition) becomes sufficient to cause the desorption of all its hydrophobic units (H. Pasch, B. Trathnigg, HPLC of Polymers, Springer-Verlag Berlin Heidelberg 1999, paragraph 5.1).

The hydrophobic character of a peptide is mainly determined by the number and nature of non-polar residues it contains and, in part, by its primary sequence and higher-order structure. Therefore, we may assume that RP-HPLC would separate GA polypeptides by their size (i.e. molar mass) and molar fraction of hydrophobic residues (e.g. alanine). This assumption was confirmed experimentally (see Example 4).

Figure 2:
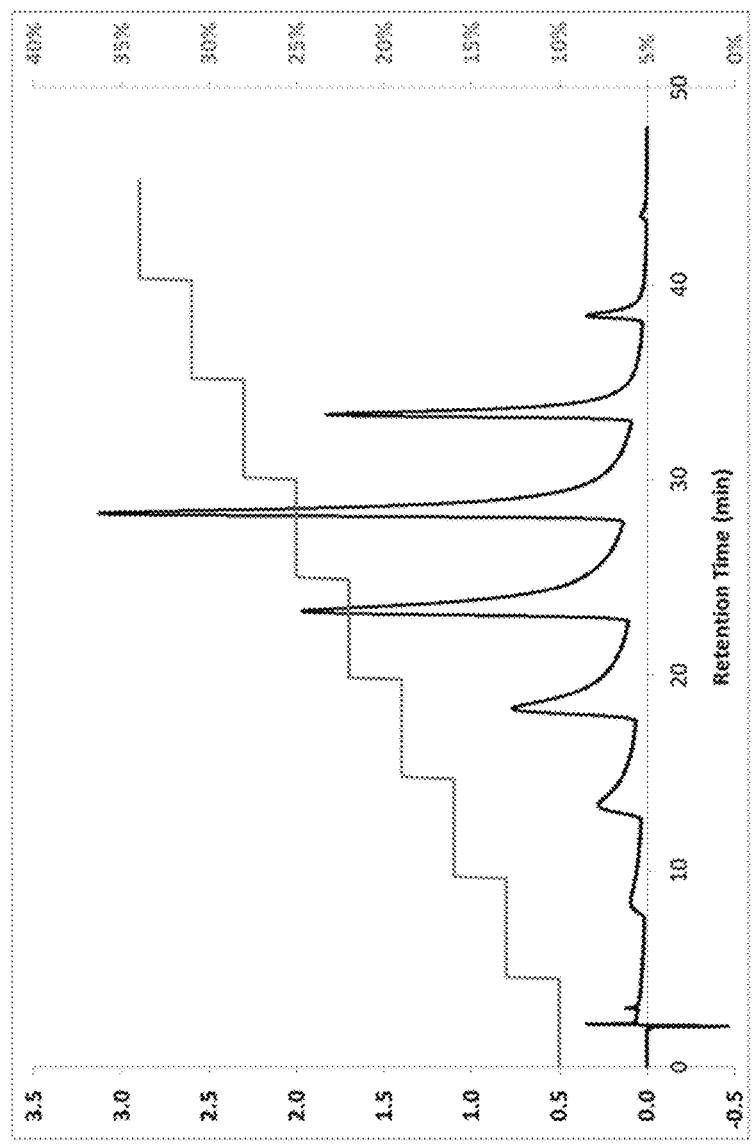
FIG. 2. RP-HPLC analysis of glatiramer acetate (stepwise gradient, see Example 3).

In RP-HPLC, gradient elution (continuous variation of the water to acetonitrile ratio) is usually preferred over isocratic elution because of higher efficiency and shorter run times. Nevertheless, in the case of GA gradient elution provides a broad, unresolved peak that is of little use for comparison studies (see FIG. 1). For this reason we developed a stepwise gradient method (a limited series of isocratic steps characterised by different water to acetonitrile ratios), which allowed the separation of a range of fractions with increasing hydrophobicity (see Example 3 and FIG. 2).

In the case of GA, a stepwise gradient method has surprisingly shown to have some important advantages over a linear gradient method:

Chromatograms can be easily integrated in order to estimate the relative abundance of species (or fractions) with different composition. In one embodiment of the invention (see Example 3) the chromatographic profile of GA samples can be quantitatively evaluated through the analysis of the peak areas of seven central fractions.

The analytical method is readily scalable to a preparative HPLC method, which allows isolating and analysing fractions with different composition (see Example 4).

The subject-matter of the present invention is therefore represented by method for analysing a mixture of polypeptides, each of which polypeptide comprises L-glutamic acid, L-alanine, L-tyrosine and L-lysine, which method comprises subjecting said mixture of polypeptides to RP-HPLC in a chromatographic column. According to the method of the present invention, the mobile phase contained in the column comprises a mixture of at least two solutions, having different polarity, namely a more polar solution and a less polar solution; in particular, according to the method of the present invention, the volume percentage of the less polar solution increases over time in a stepwise manner (and, consequently, the volume percentage of the more polar solution decreases over time in a stepwise manner).

According to an embodiment of the invention, the more polar solution is an aqueous solution; preferably, it consists of water.

According to an embodiment of the invention, the less polar solution contains at least one water-miscible organic solvent, which may be selected from acetonitrile and $C_1$-$C_3$ alcohols; preferably, it consists of acetonitrile.

According to an embodiment of the invention, the volume percentage of the less polar solution increases by 2 to 4% every 4 to 6 minutes; according to a preferred embodiment, the volume percentage of the less polar solution increases by 3% every 4.5 to 5.5 minutes.

The stationary phase of the chromatographic column, which can be used in the method of the present invention may be an alkyl-bonded silica gel, preferably a C4-bonded silica gel; such a chromatographic column may be equipped with a UV detector.

The method of the present invention may include determining the chemical composition distribution and/or the hydrophobic character of the mixture of polypeptides, which is subjected to RP-HPLC analysis.

According to an embodiment of the invention, the mixture of polypeptides which is subjected to RP-HPLC analysis is a glatiramoid or a pharmaceutically acceptable salt thereof, preferably glatiramer acetate. In such a mixture of polypeptides, the molar fraction range of L-glutamic acid may be 0.129-0.153, that of L-alanine may be 0.392-0.462, that of L-tyrosine may be 0.086-0.100 and that of L-lysine may be 0.300-0.374; preferably the average molar fraction of L-glutamic acid is about 0.141, that of L-alanine is about 0.427, that of L-tyrosine is about 0.095 that and of L-lysine is about 0.338.

The subject-matter of the present invention further includes a process for manufacturing a mixture of polypeptides, which comprises a method for analysing a mixture of polypeptides as disclosed above.

The following examples have the purpose of further illustrating the invention without however limiting it.

Example 1

GA was prepared by the method previously described (Teitelbaum et al. 1971, U.S. Pat. Nos. 3,849,550, 5,800,808) which include the following steps:

Polymerisation of the Protected Amino Acid Monomers

The N-carboxyanhydrides (NCAs) of γ-benzyl glutamate (35 g), alanine (50 g), tyrosine (18 g) and trifluoroacetyl lysine (83 g) are dissolved in 3.5 liters of anhydrous dioxane. The polymerisation process is initiated by the addition of a proper amount of diethylamine. The reaction mixture is stirred at room temperature for 24 hours and then poured into 10 liters of purified water. The product is filtered, washed with water and dried to obtain a batch of protected copolymer.

Deprotection of Gamma-Benzyl Glutamate and Partial Depolymerisation

The protected copolymer mixture is treated with a solution of hydrobromic acid (33%) in acetic acid, which removes the benzyl protecting group from the side chain of the glutamate residue and cleaves the polymer to smaller chains. The time needed to obtain a mixture of proper average molecular weight depends on the reaction temperature and the size of protected copolymer. A small scale test reaction is thus performed on every new batch: at different time periods (e.g. every hour) the average molecular weight is determined by SEC analysis, after removal of the remaining TFA group; a curve of molecular weight against the reaction time is drawn, and the time needed for obtaining the target value is calculated and applied to the large scale reaction. The product obtained by the large scale reaction is finally poured into excess water, filtered, washed and dried, yielding the TFA-protected copolymer.

Deprotection of N-Trifluoroacetyl Lysine in Aqueous Piperidine

TFA-protected copolymer is suspended in an aqueous solution of piperidine (1 mol/l) at a concentration of about 18 g/l. The mixture is stirred for 24 hours at room temperature and filtered. The solution of crude copolymer is ultrafiltered against water until a pH=8 is attained. Then acetic acid is added to the solution to have a pH in the range 4.0-4.5, and the copolymer is further ultrafiltered against water until its pH is in the range 5.5-6.0. This solution is then concentrated and freeze dried to obtain a batch of solid glatiramer acetate.

Example 2

Deviating samples were prepared by deliberately altering the "standard conditions" employed for the manufacturing of GA. In particular:

Deviating sample A (low molecular weight copolymer) was obtained by increasing the reaction temperature during the depolymerisation step.

Deviating sample B (altered composition) was obtained by employing a deficit of L-alanine (−10%) during the polymerisation step.

Deviating sample C (altered composition) was obtained by employing an excess of L-lysine (+20%) during the polymerisation step.

Deviating sample D (altered amino acid sequences) was obtained by polymerising the NCAs in dimethylformamide. The use of a polar aprotic solvent alters the polymerisation kinetics and ultimately the sequences of the intermediate copolymer chains.

Example 3

Analyses were performed on a 1260 Infinity LC System (Agilent Technologies) equipped with four modules: binary pump (model G1312A), degasser (model G1322A), autosampler (model G1367B) and diode array detector (model G1315D). The instrument was located in a temperature-controlled laboratory (temperature: 24° C.). Chromatograms were registered and processed using the software ChemStation for LC 3D Systems (Agilent Technologies).

Operating Conditions:

Solvent A: Milli-Q water with TFA 0.10% (v/v);
Solvent B: acetonitrile with TFA 0.08% (v/v);
Chromatographic column: XBridge Protein BEH C4 from Waters (pore size: 300 Å, particle size: 3.5 μm; dimensions: 4.6×150 mm);
Sample concentration: 10 mg/ml
Injection volume: 10 μl;
Flow rate: 1.00 ml/min;
Stepwise gradient: see Table 1;
Detector: UV at 220 nm;
Gradient time: 45.40 minutes;
Total run time: 57.50 minutes.

TABLE 1

| | Stepwise gradient | | | |
|---|---|---|---|---|
| Step | Total Time (min) | Flow Rate (μl/min) | A (%) | B (%) |
| 0 | 0.00 | 1000 | 90.0 | 10.0 |
| 1 | 4.50 | 1000 | 90.0 | 10.0 |
| 2 | 4.60 | 1000 | 87.0 | 13.0 |
| 3 | 9.60 | 1000 | 87.0 | 13.0 |

TABLE 1-continued

Stepwise gradient

| Step | Total Time (min) | Flow Rate (μl/min) | A (%) | B (%) |
|---|---|---|---|---|
| 4 | 9.70 | 1000 | 84.0 | 16.0 |
| 5 | 14.70 | 1000 | 84.0 | 16.0 |
| 6 | 14.80 | 1000 | 81.0 | 19.0 |
| 7 | 19.80 | 1000 | 81.0 | 19.0 |
| 8 | 19.90 | 1000 | 78.0 | 22.0 |
| 9 | 24.90 | 1000 | 78.0 | 22.0 |
| 10 | 25.00 | 1000 | 75.0 | 25.0 |
| 11 | 30.00 | 1000 | 75.0 | 25.0 |
| 12 | 30.10 | 1000 | 72.0 | 28.0 |
| 13 | 35.10 | 1000 | 72.0 | 28.0 |
| 14 | 35.20 | 1000 | 69.0 | 31.0 |
| 15 | 40.20 | 1000 | 69.0 | 31.0 |
| 16 | 40.30 | 1000 | 66.0 | 34.0 |
| 17 | 45.30 | 1000 | 66.0 | 34.0 |
| 18 | 45.40 | 1000 | 20.0 | 80.0 |
| 19 | 49.40 | 1000 | 20.0 | 80.0 |
| 20 | 49.50 | 1000 | 90.0 | 10.0 |
| 21 | 57.50 | 1000 | 90.0 | 10.0 |

For each sample, six consecutive replicate analyses were run. Sample analyses were alternated to blank and placebo analyses. After placebo subtraction, each chromatogram was integrated and the peak areas were normalised to the total area, the latter being the area of all the seven peaks (see FIG. 2). For each sample, the average peak areas (calculated over six replicates) were reported.

TABLE 2

Results of RP-HPLC analyses of Copaxone and four deviating samples. Out-of-specification parameters are highlighted in bold character.

| Sample | Peak 1 Area % | Peak 2 Area % | Peak 3 Area % | Peak 4 Area % | Peak 5 Area % | Peak 6 Area % | Peak 7 Area % |
|---|---|---|---|---|---|---|---|
| P63037 | 2.8 | 7.0 | 15.2 | 27.7 | 29.0 | 14.5 | 3.8 |
| X07181 | 3.2 | 7.9 | 16.2 | 27.9 | 28.5 | 13.2 | 3.0 |
| X06251 | 3.2 | 7.6 | 15.5 | 27.9 | 29.5 | 13.4 | 2.9 |
| P53886 | 3.5 | 8.2 | 16.8 | 28.1 | 27.8 | 12.7 | 2.8 |
| P53890 | 2.8 | 7.5 | 16.6 | 28.9 | 28.6 | 12.8 | 2.7 |
| X05981 | 2.6 | 6.6 | 14.8 | 27.9 | 30.5 | 14.5 | 3.1 |
| MIN | 2.6 | 6.6 | 14.8 | 27.7 | 27.8 | 12.7 | 2.7 |
| MAX | 3.5 | 8.2 | 16.8 | 28.9 | 30.5 | 14.5 | 3.8 |
| A | 5.7 | 11.1 | 19.7 | 28.3 | 23.4 | 9.6 | 2.2 |
| B | 4.5 | 9.8 | 19.6 | 32.1 | 25.8 | 7.4 | 0.9 |
| C | 9.2 | 16.6 | 25.8 | 28.8 | 15.7 | 3.5 | 0.4 |
| D | 3.9 | 6.4 | 10.0 | 18.0 | 27.3 | 24.2 | 10.3 |

Six batches of Teva's Copaxone and four deviating samples (A to D, see Example 2) were analysed through the method described above. Comparison of the results (reported in Table 2; out-of-specification parameters are highlighted in bold character) show that the analytical method is able to distinguish glatiramer acetate from non-conforming copolymers obtained by altering:

The duration and/or the temperature of the cleavage reaction, and therefore the average molecular weight of the copolymer (sample A);

The bulk amino acid composition and ultimately the hydrophobicity of the resultant polypeptide mixture (samples B and C);

The amino acid sequences of the intermediate (protected) copolymer chains (sample D).

Example 4

The semi-preparative fractionation of glatiramer acetate samples was carried out using the stepwise gradient method, described in Example 3, conveniently optimised for semi-preparative chromatography.

Experiments were performed on a Waters assembled equipment of six modules: a multi-solvent delivery system (600S Controller), an high-capacity sample processing system (2767 Sampler Manager), the Column Fluidics Organizer, a pulse-dampened pump for post-column application (Reagent Manager), a UV detector (2487 Dual Absorbance Detector), and a mass spectrometer (MicromassZQ). All these modules were controlled by MassLynx MS Software (Waters Corporation).

Operating Conditions:
Solvent A: Milli-Q water with TFA 0.10% (v/v);
Solvent B: acetonitrile with TFA 0.08% (v/v);
Chromatographic column: Jupiter C4 AXIA from Phenomenex (pore size: 300 Å, particle size: 10 μm; dimensions: 21.2×150 mm);
Sample concentration: 20 mg/ml
Injection volume: 950 μl;
Flow rate: 20.00 ml/min;
Stepwise gradient: see Table 1;
Detector: UV at 220 nm;
Gradient time: 45.40 minutes;
Total run time: 57.50 minutes.

A batch of Copaxone (#X07181) was fractionated six times according to the procedure described above. The fractions collected (corresponding to peaks 3 to 6, see FIG. 2) were dried under vacuum and subsequently analysed for determining their amino acid content. Samples were hydrolysed in 6 N HCl/H$_2$O. Then, the amino acids were derivatised (in order to get volatile derivatives), and gas chromatographically separated on a capillary column.

Figure 3:
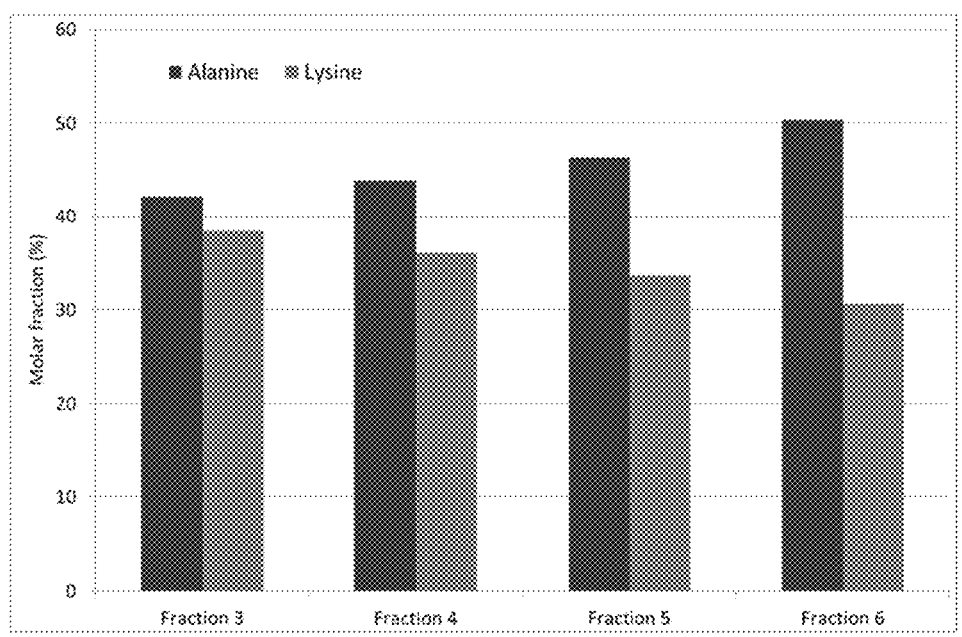
FIG. 3. Amino acid composition (expressed as L-alanine and L-lysine molar fractions) of the four central fractions (see Example 4).

The results of amino acid analysis (see Table 3 and FIG. 3) confirm (experimentally) that the molar fraction of L-alanine ($X_A$) increases with the retention time (and hydrophobicity) of the polypeptides, whereas the molar fraction of L-lysine ($X_K$) decreases. As a result, the $X_A/X_K$ ratio correlates to polypeptides' hydrophobicity.

TABLE 3

Amino acid molar fractions (%) and $X_A/X_K$ ratio of fractions 3-6 determined for six replicate fractionations of Copaxone (batch # X07181).

| Fraction | $X_A$ (%) | $X_K$ (%) | $X_Y$ (%) | $X_E$ (%) | $X_A/X_K$ |
|---|---|---|---|---|---|
| 3 | 42.4 | 38.5 | 9.4 | 9.8 | 1.10 |
| 3 | 41.3 | 38.3 | 9.4 | 11.0 | 1.08 |
| 3 | 43.0 | 38.3 | 9.5 | 9.2 | 1.12 |
| 3 | 42.1 | 38.3 | 9.5 | 10.1 | 1.10 |
| 3 | 42.1 | 38.7 | 9.3 | 9.9 | 1.09 |
| 3 | 41.3 | 38.6 | 9.4 | 10.7 | 1.07 |
| 4 | 44.0 | 35.8 | 9.5 | 10.7 | 1.23 |
| 4 | 43.2 | 36.0 | 9.5 | 11.3 | 1.20 |
| 4 | 45.4 | 35.4 | 9.6 | 9.6 | 1.28 |
| 4 | 43.5 | 36.2 | 9.5 | 10.8 | 1.20 |
| 4 | 43.3 | 36.4 | 9.4 | 11.0 | 1.19 |
| 4 | 43.7 | 36.6 | 9.4 | 10.3 | 1.19 |
| 5 | 46.9 | 33.1 | 9.3 | 10.7 | 1.42 |
| 5 | 46.4 | 33.2 | 9.4 | 11.1 | 1.40 |
| 5 | 45.5 | 34.1 | 9.3 | 11.1 | 1.33 |
| 5 | 45.1 | 33.6 | 9.4 | 11.8 | 1.34 |
| 5 | 46.7 | 33.9 | 9.2 | 10.3 | 1.38 |
| 5 | 47.1 | 34.0 | 9.2 | 9.7 | 1.39 |
| 6 | 49.7 | 30.5 | 9.0 | 10.8 | 1.63 |
| 6 | 49.3 | 30.6 | 8.9 | 11.2 | 1.61 |

TABLE 3-continued

Amino acid molar fractions (%) and $X_A/X_K$ ratio of fractions 3-6 determined for six replicate fractionations of Copaxone (batch # X07181).

| Fraction | $X_A$ (%) | $X_K$ (%) | $X_Y$ (%) | $X_E$ (%) | $X_A/X_K$ |
|---|---|---|---|---|---|
| 6 | 53.0 | 30.2 | 9.0 | 7.8 | 1.75 |
| 6 | 48.9 | 30.8 | 9.0 | 11.3 | 1.59 |
| 6 | 51.7 | 30.2 | 9.0 | 9.1 | 1.71 |
| 6 | 49.6 | 31.3 | 8.8 | 10.4 | 1.58 |

The invention claimed is:

1. A method for analyzing a mixture of polypeptides, said method comprising the following steps,
    a) subjecting said mixture of polypeptides to analytical reversed-phase high-performance liquid chromatography, with a mobile phase comprising a mixture of at least two solutions having different polarity, a more polar solution and a less polar solution, wherein the less polar solution has a volume percentage that increases over time in a stepwise manner; and
    b) recording a chromatogram on a chromatographic system equipped with a suitable detector,
    wherein said mixture of polypeptides contains four specific amino acids: L-glutamic acid, L-alanine, L-tyrosine and L-lysine, in defined molar fraction ranges.

2. The method according to claim 1, wherein the volume percentage of the less polar solution increases by 2 to 4% every 4 to 6 minutes.

3. The method according to claim 2, wherein the volume percentage of the less polar solution increases by 3% every 4.5 to 5.5 minutes.

4. The method according to claim 2, wherein the volume composition of the mobile phase changes volume composition over time as reported in the following table, wherein A represents the volume percentage of the more polar solution and B represents the volume percentage of the less polar solution:

| Step | Total Time (min) | Flow Rate (μl/min) | A (%) | B (%) |
|---|---|---|---|---|
| 0 | 0.00 | 1000 | 90.0 | 10.0 |
| 1 | 4.50 | 1000 | 90.0 | 10.0 |
| 2 | 4.60 | 1000 | 87.0 | 13.0 |
| 3 | 9.60 | 1000 | 87.0 | 13.0 |
| 4 | 9.70 | 1000 | 84.0 | 16.0 |
| 5 | 14.70 | 1000 | 84.0 | 16.0 |
| 6 | 14.80 | 1000 | 81.0 | 19.0 |
| 7 | 19.80 | 1000 | 81.0 | 19.0 |
| 8 | 19.90 | 1000 | 78.0 | 22.0 |
| 9 | 24.90 | 1000 | 78.0 | 22.0 |
| 10 | 25.00 | 1000 | 75.0 | 25.0 |
| 11 | 30.00 | 1000 | 75.0 | 25.0 |
| 12 | 30.10 | 1000 | 72.0 | 28.0 |
| 13 | 35.10 | 1000 | 72.0 | 28.0 |
| 14 | 35.20 | 1000 | 69.0 | 31.0 |
| 15 | 40.20 | 1000 | 69.0 | 31.0 |
| 16 | 40.30 | 1000 | 66.0 | 34.0 |
| 17 | 45.30 | 1000 | 66.0 | 34.0 |
| 18 | 45.40 | 1000 | 20.0 | 80.0 |
| 19 | 49.40 | 1000 | 20.0 | 80.0 |
| 20 | 49.50 | 1000 | 90.0 | 10.0 |
| 21 | 57.50 | 1000 | 90.0 | 10.0. |

5. The method according to claim 1, further comprising a chromatographic column with a stationary phase being an alkyl-bonded silica gel.

6. The method according to claim 5, wherein said alkyl-bonded silica gel is a C4-bonded silica gel.

7. The method according to claim 1, wherein the suitable detector is an UV detector.

8. The method according to claim 1, which further comprises determining relative abundance of fractions having different amino acid composition and/or hydrophobic character.

9. The method according to claim 1, wherein said mixture of polypeptides is a glatiramoid or a pharmaceutically acceptable salt thereof.

10. The method according to claim 9, wherein said mixture of polypeptides is glatiramer acetate.

11. The method according to claim 1, wherein said molar fraction ranges are 0.129-0.153 for L-glutamic acid, 0.392-0.462 for L-alanine, 0.086-0.100 for L-tyrosine and 0.300-0.374 for L-lysine.

12. The method according to claim 11, wherein, in said mixture of polypeptides, L-glutamic acid has an average molar fraction of about 0.141, L-alanine has an average molar fraction of about 0.427, L-tyrosine has an average molar fraction of about 0.095, and L-lysine has an average molar fraction of about 0.338.

13. A process for manufacturing a mixture of polypeptide analyzed with the method according to claim 1.

* * * * *